US00PP11468P

United States Patent [19]

van Rijn

[11] Patent Number: Plant 11,468

[45] Date of Patent: Aug. 1, 2000

[54] ANTHURIUM PLANT NAMED 'BABY RED'

[75] Inventor: Leonardus van Rijn, Schipluiden, Netherlands

[73] Assignee: Rijnplant B.V., Schipluiden, Netherlands

[21] Appl. No.: 09/177,593

[22] Filed: Oct. 22, 1998

[51] Int. Cl.[7] ..... A01H 5/00

[52] U.S. Cl. ..... Plt./365

[58] Field of Search ..... Plt./365, 369

*Primary Examiner*—Lynette R. F. Smith
*Assistant Examiner*—Kent L. Bell
*Attorney, Agent, or Firm*—C. A. Whealy

[57] ABSTRACT

A distinct cultivar of Anthurium plant named 'Baby Red', characterized by its compact, upright, outwardly arching and very freely clumping growth habit; strong rooting system; small dark green leaves that are ovate in shape; numerous inflorescences that are positioned upright and above the foliage on strong and erect scapes; durable red spathes; year-round continuous flowering; and good post-production longevity.

2 Drawing Sheets

BACKGROUND OF THE INVENTION

The present invention relates to a new and distinct cultivar of Anthurium plant, botanically known as *Anthurium andreanum*, and hereinafter referred to by the cultivar name 'Baby Red'.

The new Anthurium is a product of a planned breeding program conducted by the Inventor in Schipluiden, The Netherlands. The objective of the program is to create new compact Anthurium cultivars that are suitable for smaller containers and have a freely clumping growth habit, strong plant growth, attractive spathe color, numerous inflorescences and leaves, and good post-production longevity.

The new Anthurium originated from a self-pollination by the Inventor on Jan. 24, 1994 of the Inventor's proprietary *Anthurium andreanum* selection code number 9325. The cultivar 'Baby Red' was discovered and selected by the Inventor as a plant within the progeny of the stated cross in a controlled environment in Schipluiden, The Netherlands in the Autumn of 1995.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Baby Red'. These characteristics in combination distinguish 'Baby Red' as a new and distinct cultivar:

1. Compact, upright, outwardly arching and very freely clumping growth habit.

2. Strong rooting system.

3. Small dark green leaves that are ovate in shape.

4. Numerous inflorescences that are positioned upright and above the foliage on strong and erect scapes.

5. Durable red spathes.

6. Year-round continuous flowering.

7. Good post-production longevity.

The new Anthurium can be compared to the parent, the Inventor's proprietary selection code number 9325. In side-by-side comparisons conducted by the Inventor in Schipluiden, The Netherlands, plants of the new Anthurium differ from plants of selection code number 9325 in the following characteristics:

1. Plants of the new Anthurium are more compact than plants of the selection code number 9325.

2. Plants of the new Anthurium are more freely clumping than plants of the selection code number 9325.

3. Plants of the new Anthurium have smaller leaves than plants of the selection code number 9325.

4. Plants of the new Anthurium have smaller spathes than plants of the selection code number 9325.

5. Plants of the new Anthurium and the selection code number 9325 differ in spathe shape.

The new Anthurium can be compared to the Anthurium cultivar 'Champion' disclosed in U.S. Plant Pat. No. 9,088. In side-by-side comparisons conducted by the Inventor in Schipluiden, The Netherlands, plants of the new Anthurium differ from plants of the cultivar 'Champion' in the following characteristics:

1. Plants of the new Anthurium are more freely clumping than plants of the cultivar 'Champion'.

2. Plants of the new Anthurium have smaller leaves than plants of the cultivar 'Champion'.

3. Plants of the new Anthurium have stronger roots than plants of the cultivar 'Champion'.

4. Plants of the new Anthurium and the cultivar 'Champion' differ in spathe color.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type.

The photograph on the first sheet comprises a top perspective view of a typical potted plant of the cultivar 'Baby Red'.

The photograph on the second sheet comprises a close-up view of a typical spathe and spadix of the cultivar 'Baby Red'. Leaf, spathe and spadix colors in the photographs appear lighter than the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe 6-month-old plants grown in Schipluiden, The Netherlands, in a glass greenhouse with an average day temperature of 25° C. and an average night temperature of 19° C.

Botanical classification: *Anthurium andreanum* cultivar 'Baby Red'.

Parentage:

*Female parent.*—Inventor's proprietary *Anthurium andreanum* selection code number 9325.

*Male parent.*—Inventor's proprietary *Anthurium andreanum* selection code number 9325.

Propagation:

*Method.*—Typically by tissue culture.

*Time to initiate roots.*—About 70 or 84 days at 24° C. or 21° C., respectively.

*Rooting habit.*—Numerous and very strong fleshy roots.

Plant description:

*Plant shape.*—Upright, inverted triangle, symmetrical.

*Growth habit.*—Erect when young, becoming outwardly arching as plants develop. Compact, freely clumping, bushy and dense. Appropriate for 9 to 20-cm containers.

*Plant height.*—About 25 cm from soil level to apex of spathes.

*Plant vigor.*—High.

*Growth rate.*—Moderate.

*Crop time.*—About 8 and 10 months are usually required from planting of young plants to finished plants in 14-cm and 17-cm containers, respectively.

*Foliage description.*—Quantity: Usually about 10 leaves per clump. Length: About 14 cm. Width: About 8.5 cm. Shape: Ovate, flat. Apex: Apiculate. Base: Rounded to cordate; lobes not overlapping. Margin: Entire, slightly undulating. Texture: Smooth, glabrous, leathery. Color: Young leaves, upper surface: Brownish red to green. Young leaves, lower surface: Brownish red to green. Mature leaves, upper surface: 137A. Mature leaves, lower surface: 143A to 144A. Petiole: Length: About 22.5 cm. Color: Brownish red to green. Geniculum length: About 2.5 cm. Geniculum color: The same as the petiole, but sometimes lighter green than petiole.

Inflorescence description:

*Inflorescence arrangement.*—Spathe with spadix held above the foliage. Flowering structures arise from leaf axils. Freely flowering; continuous flowering year-round; typically about 20 inflorescences per plant. Not fragrant.

*Inflorescence longevity.*—Inflorescences last about six weeks under winter conditions and up to three months under summer conditions; persistent.

*Flowers.*—Quantity per spadix: Numerous, about 150 flowers. Shape: Rounded. Diameter: About 1 mm, maximum.

*Spathe.*—Length: About 7 cm. Width: About 6.25 cm. Height above foliage: About 2.5 cm. Shape: Deltoid to cordate. Apex: Cuspidate to mucronate. Base: Rounded; lobes not overlapping. Margin: Entire. Texture: Leathery, glabrous, very slight blistering, shiny. Color: When opening: 45A to 45B. Front surface: 45A. Back surface: 52A to 52B. After senescence: 47B to 47C.

*Spadix.*—Length: About 3.75 cm. Diameter: About 7.5 mm. Shape: Columnar. Cross section: Rounded. Longitudinal axis: Weakly recurved. Color: Base: Creamy white. Mid-section: Close to 29B. Apex: 44C to 29B. Color, after senescence: 29B.

*Scape.*—Length: About 25 cm. Aspect: Strong and erect. Color: At base, green, 144A to 146A, with anthocyanin towards apex.

*Reproductive organs.*—Androecium: Pollen color: Creamy white. Gynoecium: Stigma shape: Ovoid.

Disease resistance: Plants of the new Anthurium have not been shown to be resistant to diseases common to Anthurium.

Seed development: Seed development on plants of the new Anthurium has not been observed.

It is claimed:

1. A new and distinct cultivar of Anthurium plant named 'Baby Red', as illustrated and described.

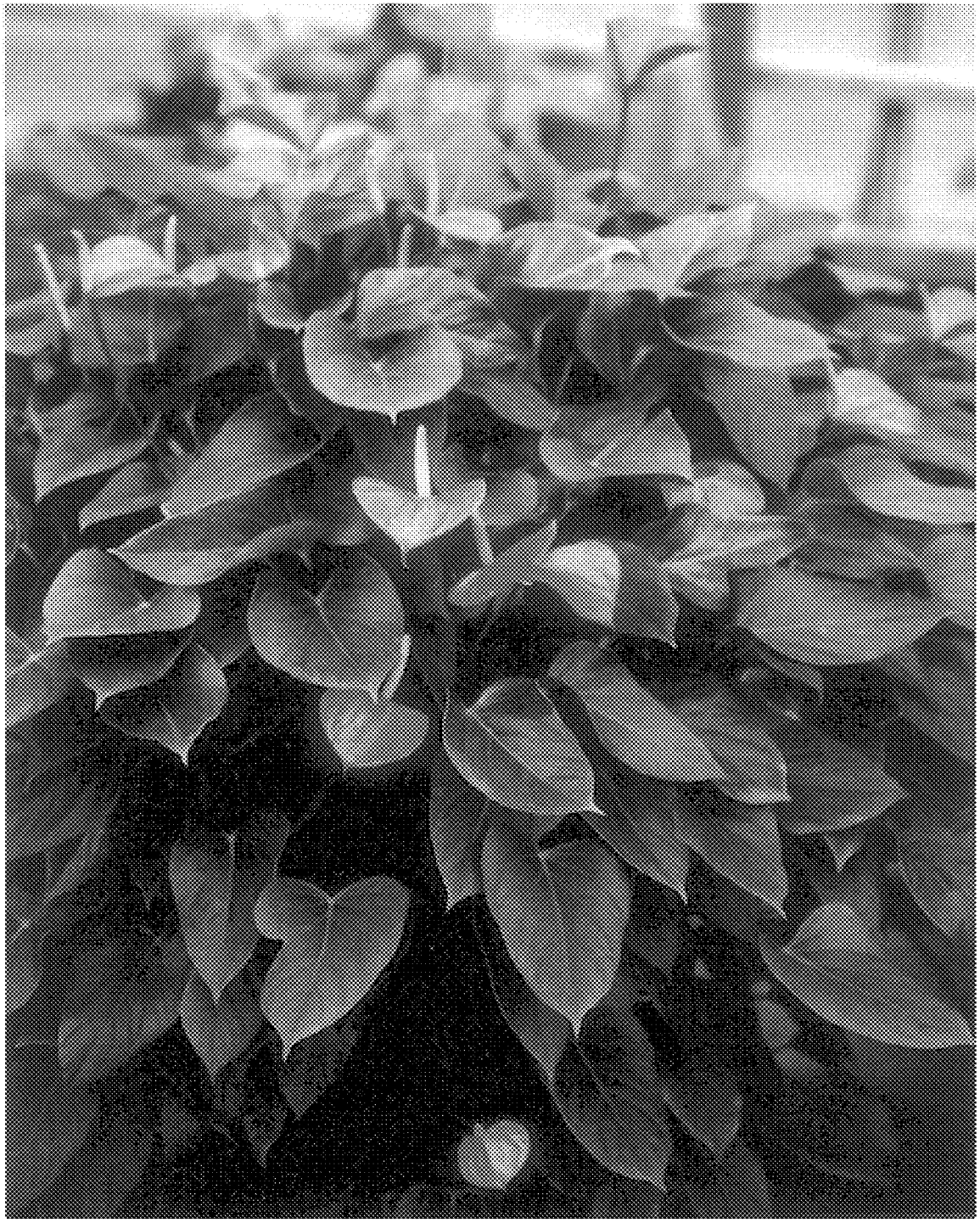

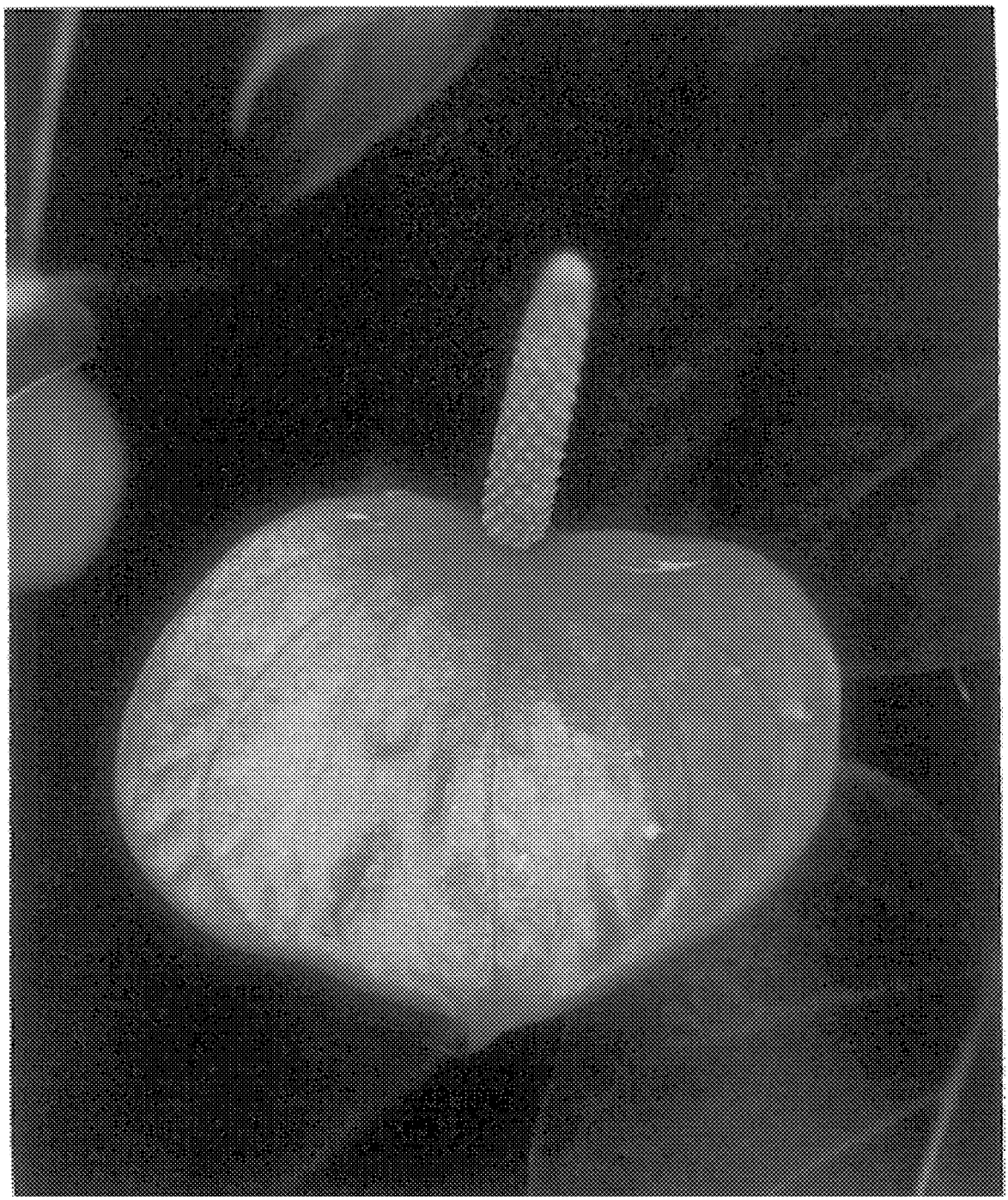

* * * * *